US008480733B2

(12) United States Patent
Navia et al.

(10) Patent No.: US 8,480,733 B2
(45) Date of Patent: Jul. 9, 2013

(54) APPARATUS AND METHODS FOR REPAIR OF A CARDIAC VALVE (75) Inventors: Jose Luis Navia, Shaker Heights, OH (US); Ji-Feng Chen, Lakewood, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 60 days.

(21) Appl. No.: 13/040,394

(22) Filed: Mar. 4, 2011

(65) Prior Publication Data
US 2011/0153009 A1 Jun. 23, 2011

Related U.S. Application Data (60) Division of application No. 11/800,454, filed on May 4, 2007, now Pat. No. 7,914,576, which is a continuation-in-part of application No. 10/850,508, filed on May 20, 2004.

(60) Provisional application No. 60/472,030, filed on May 20, 2003, provisional application No. 60/547,416, filed on Feb. 23, 2004.

(51) Int. Cl.
*A61F 2/24* (2006.01)

(52) U.S. Cl.
USPC .......................... 623/2.36; 623/2.37

(58) Field of Classification Search
USPC ................................ 623/2.36–2.39
See application file for complete search history.

(56) References Cited

U.S. PATENT DOCUMENTS

| | | | |
|---|---|---|---|
| 5,843,164 A * | 12/1998 | Frantzen et al. | 623/1.16 |
| 5,855,601 A * | 1/1999 | Bessler et al. | 623/2.38 |
| 5,888,240 A | 3/1999 | Carpentier et al. | |
| 5,954,761 A | 9/1999 | Machek et al. | |
| 6,022,369 A | 2/2000 | Jacobsen et al. | |
| 6,290,728 B1 * | 9/2001 | Phelps et al. | 623/23.7 |

(Continued)

FOREIGN PATENT DOCUMENTS

| | | |
|---|---|---|
| EP | 1 348 406 A1 | 10/2003 |
| WO | WO-03/028558 A2 | 4/2003 |
| WO | WO-03/088875 A1 | 10/2003 |
| WO | WO-03/105730 A1 | 12/2003 |

OTHER PUBLICATIONS

Dagum et al., Functional Evaluation of the Medtronic Stentless Porcine Xenograft Mitral Valve in Sheep, *Circulation.* 1999; 100[suppl II]:II-70-II-77.

*Primary Examiner* — Suzette J Gherbi
(74) *Attorney, Agent, or Firm* — Tarolli, Sundheim, Covell & Tummino LLP (57) ABSTRACT

An apparatus for repairing a cardiac valve includes an annuloplasty ring having an expandable support member with oppositely disposed proximal and distal end portions and a main body portion between the end portions. The proximal end portion includes a plurality of wing members extending from the main body portion. Each of the wing members includes at least one hook member for embedding into a cardiac wall and a valve annulus to secure the annuloplasty ring therein. The apparatus also includes an energy delivery mechanism for selectively contracting the annuloplasty ring to restrict the valve annulus and correct valvular insufficiency. The energy delivery mechanism includes a detachable electrical lead having distal and proximal end portions. The distal end portion has a securing member for operably attaching the distal end portion to a portion of the expandable support member. The proximal end portion is operably connected to an energy delivery source.

13 Claims, 10 Drawing Sheets

U.S. PATENT DOCUMENTS

| | | |
|---|---|---|
| 6,327,772 B1 * | 12/2001 | Zadno-Azizi et al. ......... 29/557 |
| 6,361,556 B1 | 3/2002 | Chuter |
| 6,406,493 B1 | 6/2002 | Tu et al. |
| 6,419,696 B1 | 7/2002 | Ortiz et al. |
| 6,579,308 B1 | 6/2003 | Jansen et al. |
| 6,616,675 B1 * | 9/2003 | Evard et al. .................. 606/155 |
| 6,805,711 B2 | 10/2004 | Quijano et al. |
| 7,063,719 B2 | 6/2006 | Jansen et al. |
| 7,311,730 B2 * | 12/2007 | Gabbay ....................... 623/2.38 |
| 7,510,577 B2 | 3/2009 | Moaddeb et al. |
| 2002/0002401 A1 | 1/2002 | McGuckin, Jr. et al. |
| 2003/0040793 A1 | 2/2003 | Marquez |
| 2003/0109924 A1 | 6/2003 | Cribier |
| 2003/0153932 A1 * | 8/2003 | Spence et al. ................ 606/153 |
| 2003/0191528 A1 * | 10/2003 | Quijano et al. .............. 623/2.37 |
| 2003/0199974 A1 | 10/2003 | Lee et al. |
| 2003/0220686 A1 | 11/2003 | Arru et al. |
| 2004/0039442 A1 | 2/2004 | St. Goar et al. |
| 2004/0049266 A1 * | 3/2004 | Anduiza et al. ............. 623/2.11 |
| 2004/0236419 A1 * | 11/2004 | Milo ............................ 623/2.36 |
| 2004/0260394 A1 * | 12/2004 | Douk et al. .................. 623/2.36 |
| 2005/0038509 A1 * | 2/2005 | Ashe ........................... 623/2.36 |
| 2005/0055087 A1 | 3/2005 | Starksen |
| 2005/0065601 A1 * | 3/2005 | Lee et al. ..................... 623/2.36 |
| 2005/0080483 A1 * | 4/2005 | Solem et al. ................. 623/2.11 |
| 2005/0165439 A1 | 7/2005 | Weber et al. |
| 2005/0177228 A1 * | 8/2005 | Solem et al. ................. 623/2.36 |
| 2005/0222669 A1 * | 10/2005 | Purdy .......................... 623/1.13 |
| 2005/0222678 A1 | 10/2005 | Lashinski et al. |
| 2005/0267572 A1 * | 12/2005 | Schoon et al. ............... 623/2.11 |
| 2005/0288776 A1 | 12/2005 | Shaoulian et al. |
| 2007/0038293 A1 | 2/2007 | St. Goar et al. |
| 2007/0239280 A1 | 10/2007 | Keith et al. |
| 2008/0015677 A1 | 1/2008 | Glossop et al. |
| 2009/0216322 A1 | 8/2009 | Le et al. |
| 2009/0234318 A1 | 9/2009 | Loulmet et al. |
| 2010/0049213 A1 | 2/2010 | Serina et al. |

* cited by examiner

APPARATUS AND METHODS FOR REPAIR OF A CARDIAC VALVE

RELATED APPLICATIONS

The present application is a divisional application of U.S. patent application Ser. No. 11/800,454, filed May 4, 2007 now U.S. Pat. No. 7,914,576, which is a continuation-in-part of U.S. patent application Ser. No. 10/850,508, filed on May 20, 2004, which claims priority from U.S. Provisional Patent Application Ser. No. 60/472,030, filed on May 20, 2003, and U.S. Provisional Patent Application Ser. No. 60/547,416, filed on Feb. 23, 2004. The subject matter of the aforementioned applications is incorporated herein by reference in their entireties.

TECHNICAL FIELD

The present invention relates to an apparatus and methods for repair of a cardiac valve, and is particularly directed to an apparatus and methods that include an annuloplasty ring for the correction of mitral valve and tricuspid valve disorders.

BACKGROUND OF THE INVENTION

There are two atrio-ventricular valves in the heart; one on the left side of the heart and one on the right side of the heart. The left side atrio-ventricular valve is the mitral valve and the right side atrio-ventricular valve is the tricuspid valve. Both of these valves are subject to damage that requires that the valve be repaired or replaced. Experience has shown that damaged valves can be surgically repaired, and that the long term results obtained from valve repair can be better than replacement of the valve.

The mitral and tricuspid valves differ significantly in anatomy. While the annulus of the mitral valve is generally D-shaped, the annulus of the tricuspid valve is more circular. The effects of the valvular dysfunction vary between the mitral valve and the tricuspid valve. Mitral valve regurgitation has more severe physiological consequences to the patient than does tricuspid valve regurgitation, a small amount of which is tolerable. In patients with valvular insufficiency, it is increasingly common surgical practice to retain the natural valves and to attempt to correct the defect. Many of these defects are associated with dilation of the valve annulus. This dilatation not only prevents competence of the valve, but also results in distortion of the normal shape of the valve orifice. Remodeling the valve annulus is therefore central to most reconstructive procedures for both the mitral and tricuspid valves.

Mitral or tricuspid valve annuloplasty is a restoration of the valve annulus, which effects full closure of the valve's leaflets by reestablishing the size and the shape of the normal mitral or tricuspid valve annulus. Surgical procedures such as annuloplasty more commonly incorporate the use of a prosthetic ring, where the ring is implanted over or within the mitral or tricuspid valve annulus.

In mitral valve insufficiency, the valve leaflets do not fully close and a certain amount of blood leaks back into the left atrium when the left ventricle contracts. As a result, the heart has to work harder by pumping not only the regular volume of the blood, but also the extra volume of blood that regurgitated back into the left atrium. The added workload creates an undue strain on the left ventricle. This strain can eventually wear out of the heart and result in morbidity when the conditions are prolonged and severe enough. Consequently, proper function of the mitral valve is critical to the pumping efficiency of the heart.

Many surgical procedures have been described to correct pathology of the valve leaflets, chordal tendineae, and, papillary muscles. In mitral valve repair, it is desirable to preserve the normal distance between the two fibrous trigones. The trigones more or less straddle the anterior leaflet portion of the mitral annulus. A significant surgical reduction of the inter-trigonal distance could cause left ventricular outflow tract obstruction. Thus, it is desirable to maintain the natural inter-trigonal distance after mitral valve surgery. Consequently, when a mitral valve is repaired, the result is generally a reduction in size of the posterior segment of the mitral valve annulus.

In a mitral valve repair, it is necessary to either diminish or constrict the involved segment of the mitral annulus so that the leaflets may coapt correctly when closing or, alternatively, to stabilize the annulus to prevent the possibility of dilatation from occurring. The latter is frequently achieved by implantation of a prosthetic ring in the supra-annular position. The purpose of the ring is to restrict and/or support the annulus to correct and/or prevent valvular insufficiency. However, it is important not to over-restrict the annulus or unacceptable valve stenosis could result.

As described above, in mitral valve repair, constriction of the mitral annulus should take place only in the area of the posterior portion of the native valve annulus. Shortening of the posterior portion of the mitral valve annulus may be accomplished by implanting an inexpansible rigid ring. With this approach, the surgeon must accurately choose the size of the ring that would prevent insufficiency, yet will not cause significant valve stenosis. A second approach uses a contractible ring that may be plicated during implantation. This approach has a disadvantage that a surgeon must accurately gauge not only the ring size to use, but also how to space the implanting sutures in the ring and the native annulus so that, when implanted, insufficiency is minimized. A third approach involves semi-expandable rings that may be contracted only in appropriate segments of the native annulus (but not in the anterior portion). The natural inter-trigonal distance should be maintained and the anterior leaflet should not be diminished in this circumstance.

In tricuspid valve repair, constriction of the annulus usually takes place in the posterior leaflet segment and in a small portion of the adjacent anterior leaflet. The septal leaflet segment is not usually required to be shortened.

Mitral and tricuspid valve disease is traditionally treated by surgical repair with an annuloplasty ring or surgical or replacement with a valve prosthesis. However, surgical valve replacement or repair is often an exacting operation that is done through a surgical technique where the thoracic cavity is opened. The operation requires use of a heart-lung machine for external circulation of the blood as the heart is stopped and opened during the surgical intervention and the artificial cardiac valves and/or annuloplasty rings are sewed in under direct vision. This operation exposes the patient to many risks especially in the elderly population. A percutaneous procedure that can be performed under local anesthesia in the cardiac catherization lab, rather than in cardiac surgery, could therefore offer tremendous benefits for these patients, many of whom have no options today. A minimally invasive surgical technique and percutaneous approach for delivering a prosthetic ring for mitral or tricuspid valve repair could be one of the most prominent tools in order to provide opportunities to treat patients with severe valvular insufficiency and/or end stage heart failure.

SUMMARY OF THE INVENTION

In accordance with one aspect of the present invention, an apparatus for repairing a cardiac valve comprises an annuloplasty ring including an expandable support member having oppositely disposed proximal and distal end portions and a main body portion between the end portions. The proximal end portion of the expandable support member comprises a plurality of wing members that extend from the main body portion. Each of the wing members includes at least one hook member for embedding into a cardiac wall and the valve annulus to secure the annuloplasty ring in the annulus of the cardiac valve. The apparatus also includes an energy delivery mechanism for selectively contracting the annuloplasty ring and thereby restricting the valve annulus to support the annulus and correct valvular insufficiency. The energy delivery mechanism includes a detachable electrical lead having distal and proximal end portions. The distal end portion has a securing member for operably attaching the distal end portion to a portion of the expandable support member. The proximal end portion is operably connected to an energy delivery source.

In accordance with another aspect of the present invention, an apparatus for repairing a cardiac valve comprises an annuloplasty ring including an expandable support member having oppositely disposed proximal and distal end portions and a main body portion between the end portions. The proximal end portion of the expandable support member comprises a plurality of wing members that extend from the main body portion. Each of the wing members includes at least one hook member for embedding into a cardiac wall and the valve annulus to secure the annuloplasty ring in the annulus of the cardiac valve. The apparatus also includes an inflatable balloon for expanding the expandable support member so that the annuloplasty ring engages the annulus of the cardiac valve. The apparatus further includes an energy delivery mechanism for selectively contracting the annuloplasty ring and thereby restricting the valve annulus to support the annulus and correct valvular insufficiency. The energy delivery mechanism includes at least one energy delivery member operably secured to a portion of said inflatable balloon. The at least one delivery member is in contact with a portion of the expandable support member.

In accordance with another aspect of the present invention, a method is provided for repairing a cardiac valve. One step of the method includes providing an annuloplasty ring having an expandable support member and an energy delivery mechanism. The energy delivering mechanism includes a detachable electrical lead having distal and proximal end portions. The distal end portion includes a securing member for attaching the distal end portion to a portion of the expandable support member, and the proximal end portion is operably connected to an energy delivery source. The securing member is attached to the portion of the expandable support member and the annuloplasty ring is placed around an inflatable balloon in a secured manner. Next, the balloon and the annuloplasty ring are inserted into an atrial chamber where the balloon is advanced until the annuloplasty ring is positioned within the annulus of the cardiac valve to be repaired. The expandable support member is expanded with the balloon so that the annuloplasty ring engages the annulus of the cardiac valve to secure the annuloplasty ring in the annulus. Electrical energy is then delivered to the annuloplasty ring via the energy delivery mechanism to secure the annuloplasty ring in the valve annulus. The balloon is collapsed and removed with the energy delivery mechanism from the atrial chamber.

In accordance with another aspect of the present invention, a method is provided for repairing a cardiac valve. One step of the method includes providing an annuloplasty ring having an expandable support member, an inflatable balloon for expanding the expandable support member, and an energy delivery mechanism. The energy delivery mechanism includes at least one energy delivery member secured to the inflatable balloon and in contact with a portion of the expandable support member. The annuloplasty ring is placed around the inflatable balloon in a secured manner and inserted into an atrial chamber. Next, the inflatable balloon is advanced until the annuloplasty ring is positioned within the annulus of the cardiac valve to be repaired. The expandable support member is then expanded with the inflatable balloon so that the annuloplasty ring engages the annulus of the cardiac valve and secures the annuloplasty ring in the annulus. Electrical energy is delivered to the annuloplasty ring via the energy delivery mechanism to secure the annuloplasty ring in the valve annulus. The inflatable balloon is then collapsed and removed from the atrial chamber.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
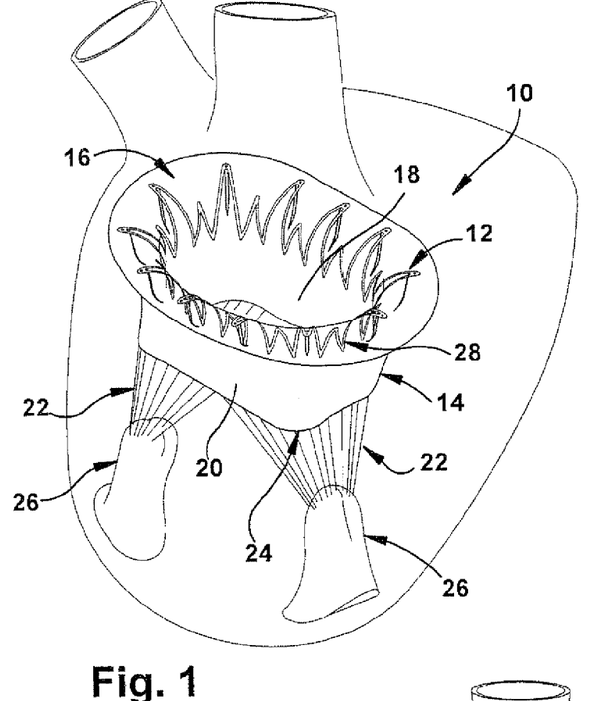
FIG. 1 is a is a schematic perspective view of a heart implanted with an annuloplasty ring for repairing a cardiac valve in accordance with the present invention.

The present invention relates to an apparatus and methods for repair of a cardiac valve. As representative of the present invention, FIG. 1 illustrates an apparatus 10 that includes an annuloplasty ring 12 for repairing a dysfunctional cardiac valve, such as a mitral valve 14. It should be understood, however, that the apparatus 10 disclosed herein could be used to repair not only a mitral valve 14, but also other cardiac valves and, in particular, a tricuspid valve (not shown).

Figure 2:
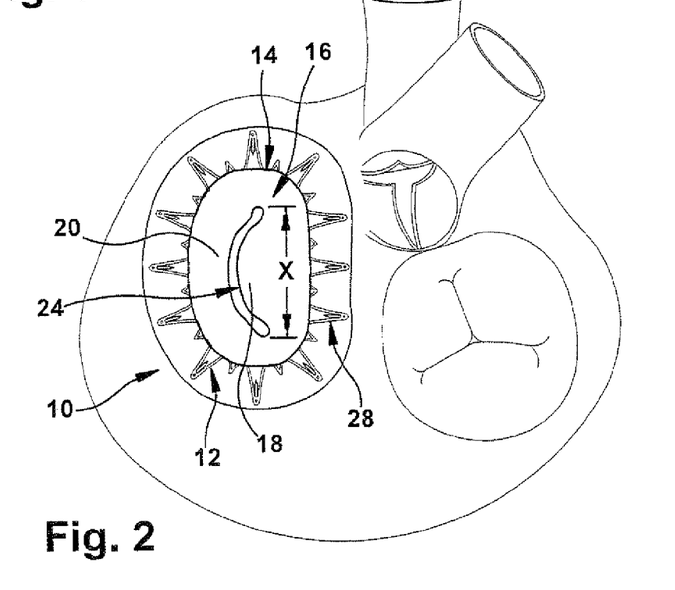
FIG. 2 is a schematic plan view of the heart and the annuloplasty ring shown in FIG. 1.

The mitral valve 14 is located between the left atrium and the left ventricle (not shown) and functions to prevent the backflow of blood from the left ventricle into the left atrium during contraction. As best seen in FIG. 2, the mitral valve 14 has a D-shaped annulus 16 that defines the opening between the left atrium and the left ventricle. The mitral valve 14 is formed by two leaflets; namely, the anterior leaflet 18 and the posterior leaflet 20. The anterior leaflet 18 extends along the generally planar base of the D-shaped valve annulus 16 between two fibrous trigones (not shown). It is desirable to maintain the distance X between the two trigones after the valve repair procedure is completed. The posterior leaflet 20 extends arcuately around the curved portion of the D-shaped annulus 16 of the mitral valve 14. Chordae tendineae 22 (FIG. 1) extend between the free edges 24 of both leaflets 18 and 20 to the papillary muscles 26 in the left ventricle.

Figure 3:
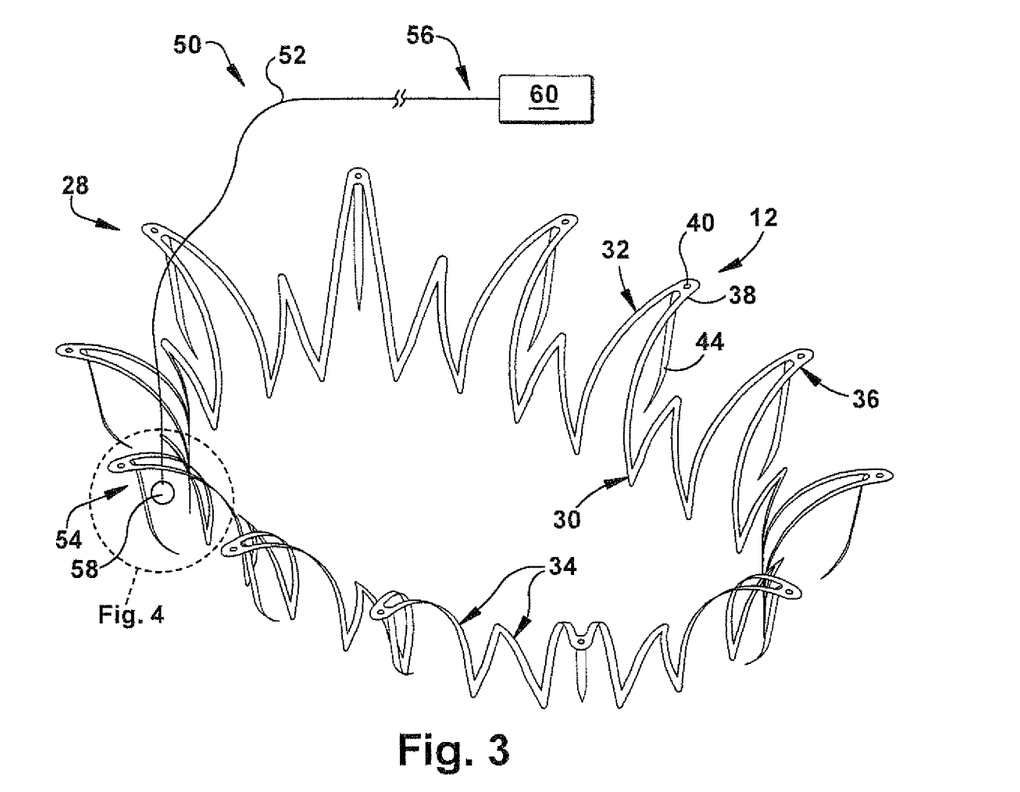
FIG. 3 is a perspective view of one embodiment of the annuloplasty ring constructed in accordance with the present invention.
Figure 4:
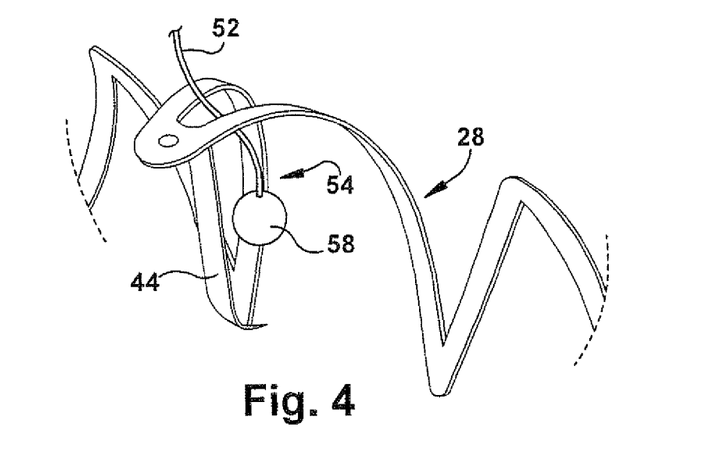
FIG. 4 is an enlarged view of a portion of FIG. 3.

One embodiment of the present invention is illustrated in FIGS. 3 and 4. As shown in FIG. 3, the apparatus 10 includes an annuloplasty ring 12 for repairing the dysfunctional mitral valve 14. The apparatus 10 comprises an expandable support member 28 that resembles a complete stent. The annuloplasty ring 12 described herein has an annular configuration that mimics the D-shape of the native annulus 16, but it will be understood by those skilled in the art that the annuloplasty ring could be a partial ring and thus have a C-shape, a U-shape, or another suitable configuration. The expandable support member 28 is both flexible and resilient, and, as discussed in more detail below, is made of a shape memory material such as Nitinol or super-elastic Nitinol. Other suitable medical grade metals or plastics having shape memory characteristics can also be used for the expandable support member 28. The flexible and expandable properties of the expandable support member 28 allow it to conform to the three-dimensional shape of the native valve annulus 16.

The expandable support member 28 comprises a continuous series of W-shaped segments, although it is contemplated that other geometries could be used. The lower tips of the W-shaped segments form a distal end portion 30 of the expandable support member 28, and the elongated upper tips of the W-shaped segments form a proximal end portion 32 of the expandable support member. For the purposes of the present invention, the term "proximal" means on the inflow or upstream side of the annuloplasty ring 12 and "distal" means on the outflow or downstream side of the annuloplasty ring. Thus, the distal end portion 30 of the expandable support member 28 is the leading edge of the expandable support member when the annuloplasty ring 12 is inserted into the body. Further, as illustrated in FIG. 7, the letter A indicates the distal direction and the letter B indicates the proximal direction.

Referring again to FIG. 3, a main body portion 34 of the expandable support member 28 is defined between the distal and proximal end portions 30 and 32. The main body portion 34 has a concave cross-sectional shape for conforming to the convex shape of the valve annulus 16. It is contemplated that the pattern of the expandable support member 28 and/or the thickness of the expandable support member in the main body portion 34 may be altered along the inter-trigonal distance X in order to maintain this distance and ensure more retraction along the posterior leaflet 20.

Figure 7:
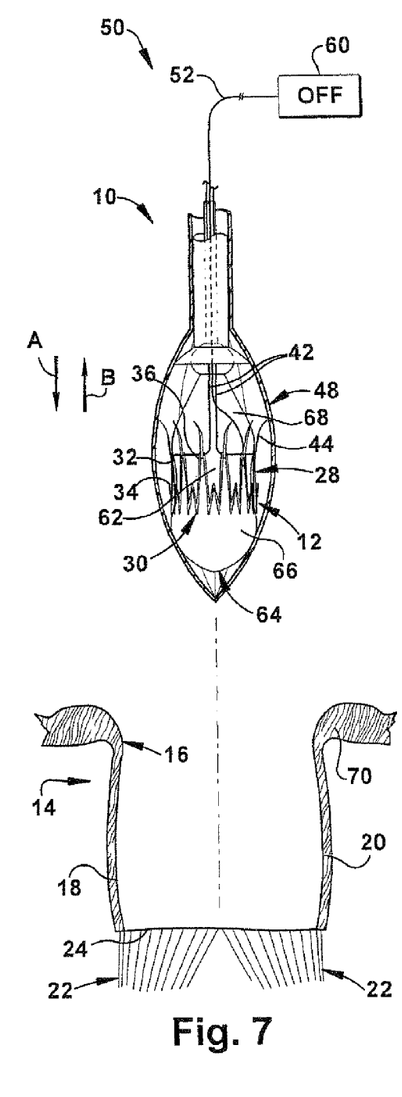
FIG. 7 is a side view, partly in section, of an apparatus for repairing a cardiac valve comprising the annuloplasty ring of FIG. 3, the apparatus being shown at an initial stage of delivery into an atrial chamber.

The proximal end portion 32 of the expandable support member 28 comprises a plurality of wing members 36 that resemble arches and which extend integrally from the main body portion 34 generally in the proximal direction B (FIG. 7). The wing members 36 (FIG. 3) also have a concave cross-sectional shape for conforming to the convex shape of the valve annulus 16. As is shown in FIGS. 7-15, the main body portion 34 and the wing members 36 are resiliently bendable from their concave cross-sectional shapes into flatter cross-sectional shapes for delivery and placement of the annuloplasty ring 12.

Figure 6:
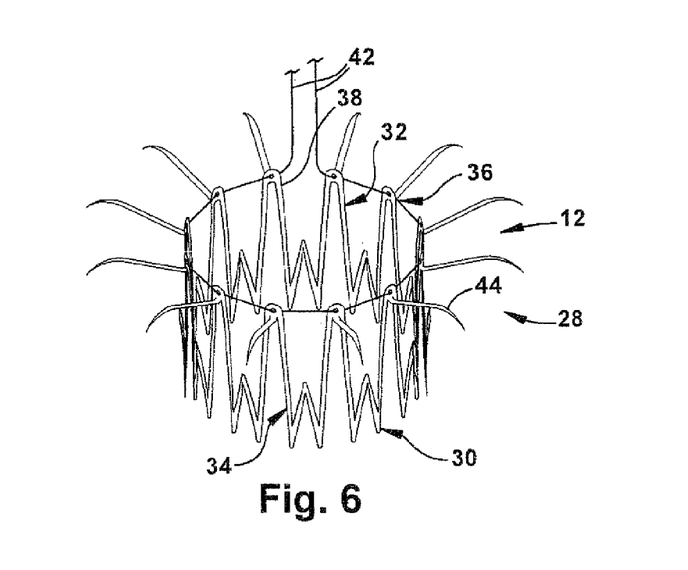
FIG. 6 is a perspective view of the annuloplasty ring with the ring being shown in a radially collapsed condition for delivery (prior to expansion by a balloon)

Each wing member 36 of the expandable support member 28 has a tip portion 38 that includes an aperture 40 for receiving a constraining wire 42 (FIG. 6). Further, the tip portion 38 (FIG. 3) of each wing member 36 includes at least one hook member 44 for embedding into a cardiac wall 70 (FIG. 7) to secure the annuloplasty ring 12 (FIG. 3) in the annulus 16 of the mitral valve 14. The hook members 44 project outward from the wing members 36 and have sharp pointed ends. It is contemplated that the pointed ends of the hook members 44 could include one or more barbs (not shown), similar to the barbs used in fishing hooks, to prevent pull-out of the hook members once they are embedded in the valve annulus 16.

As mentioned above, the expandable support member 28 is made from a shape memory material, such as super-elastic Nitinol, that is responsive to changes in temperature above and below a predetermined temperature transition range of about 75-95° F., for example. It should be understood, however, that other temperature transition ranges can be used. The expandable support member 28 has a first configuration when its temperature is below the predetermined temperature transition range and a second configuration when heated above the predetermined temperature transition range. In accordance with one aspect of the present invention, the annuloplasty ring 12 is inserted into the annulus 16 of the mitral valve 14 in the first configuration, which is an expanded condition, and is thereafter heated above the predetermined temperature transition range to change the expandable support member 28 into the second configuration, which is a contracted condition that is the desired pre-shape memorized by the material.

Figure 5:
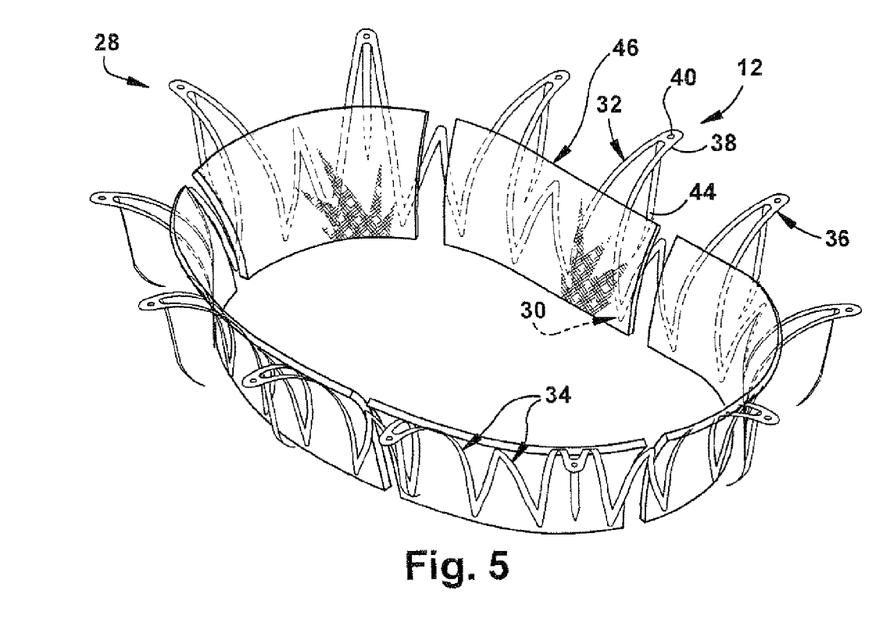
FIG. 5 is a perspective view illustrating an alternative construction for the annuloplasty ring.

FIG. 5 illustrates the annuloplasty ring 12 with a layer 46 of biocompatible material covering sections of the distal end portion 30 and the main body portion 34 of the expandable support member 28. The layer 46 of biocompatible material may be a synthetic such as DACRON®, woven velour, polyurethane, PTFE, or heparin-coated fabric. Alternatively, the layer 46 may be a biological material such as bovine or equine pericardium, a homograft, patient graft, or a cell-seeded tissue. The layer 46 can cover either the inside surface of the expandable support member 28, the outside surface of the expandable support member, or can be wrapped around both the inside and outside surfaces. The layer 46 may be attached around the entire circumference of the expandable support member 28 or, alternatively, may be attached in sections as shown in FIG. 5 to allow the expandable support member to more easily expand and contract.

The apparatus 10 further comprises a releasable constraining wire 42 (FIG. 6) for temporarily holding the wing members 36 in the flatter cross-sectional shape shown in FIGS. 8-11 during delivery and placement of the annuloplasty ring 12. The constraining wire 42 can be made from a variety of different materials including metals, polymers, synthetics, fabrics, and biological tissues. As illustrated in FIGS. 8-11, the hook members 44 extend generally radially when the wing members 36 are being held in the flatter cross-sectional shape by the constraining wire 42. However, as shown in FIG. 7, the hook members 44 are resiliently bendable to extend proximally inside a delivery capsule 48 during delivery of the annuloplasty ring 12 into the valve annulus 16. It should be understood that the delivery capsule 48 could have a variety of configurations, including a sleeve or sheath.

As shown in FIG. 3, the apparatus 10 also comprises an energy delivery mechanism 50 for selectively contracting the annuloplasty ring 12 and thereby restricting the valve annulus 16 to support the annulus and correct valvular insufficiency. The energy delivery mechanism 50 comprises a detachable electrical lead 52 having distal and proximal end portions 54 and 56. The electrical lead 52 can comprise a wire, for example, capable of conducting an electrical current. It will be appreciated that the term "wire" is a broad term having its normal and customary meaning and includes, for example, mesh, flat, round, rod-shaped, or band-shaped members. The electrical lead 52 is made of an electrically conductive material, such as platinum, platinum-iridium, stainless steel, copper, conductive polymer, or the like.

The distal end portion 54 of the electrical lead 52 includes a securing member 58 for operably attaching the distal end portion to a portion of the expandable support member 28. The securing member 58 includes a ball or sphere-shaped member securely attached to the electrical lead 52. It will be appreciated that the securing member 58 may have any other known shape or configuration, such as block or rod-shaped configuration, for example. As shown in FIG. 4, the distal end portion 54 of the electrical lead 52 is slidably received near the tip portion 38 of one wing member 36. It will also be appreciated that the distal end portion 54 of the electrical lead 52 may have a variety of other configurations. For example, the distal end portion 54 may have a spliced or forked configuration for being slidably received at the tip portion 38 of a plurality of wing members 36. As described in more detail below, the configuration of the distal end portion 54 ensures that the electrical lead 52 remains operably attached to the annuloplasty ring 12 while the annuloplasty ring is being deployed and, further, that the electrical lead can be easily detached from the expandable support member 28 after deployment.

As shown in FIG. 3, the proximal end portion 56 of the electrical lead 52 is operably connected to an energy delivery source 60. As described in greater detail below, electrical energy is delivered to the electrical lead 52 and then conducted to the expandable support member 28 so that the expandable support member obtains a temperature above the pre-determined temperature transition range and transitions from the first configuration to the second configuration. Examples of suitable energy delivery sources 60 include sources capable of delivering radio frequency (RF) energy, x-ray energy, microwave energy, ultrasonic energy such as focused ultrasound, high intensity focused ultrasound energy, light energy, electric field energy, magnetic energy, combinations of the same, or the like.

To repair the mitral valve 14 with the apparatus 10 using a percutaneous (or intravascular) approach, the annuloplasty ring 12 is properly sized for the mitral valve by the surgical team using fluoroscopic and/or echocardiographic data. The annuloplasty ring 12 may be cooled using a cryogenic source or other suitable means to place the expandable support member 28 in its first configuration.

The annuloplasty ring 12 is next positioned about the center section 62 of an inflatable balloon 64. The inflatable balloon 64 has an hourglass shape defined by first and second bulb sections 66 and 68 connected by the center section 62. Each of these sections 62, 66 and 68 may have a D-shaped diameter (or other shaped diameter) to match the D-shaped diameter of the valve 14 and the annuloplasty ring 12. The center section 62 of the balloon 64 has a smaller diameter than the bulb sections 66 and 68. The first and second bulb sections 66 and 68 and the center section 62 may be inflated together or separately. Further, the sections 62, 66 and 68 may have multiple chambers to accommodate multiple fluids (i.e., an inflation fluid and a cooling fluid). It is contemplated that the annuloplasty ring 12 could alternatively, or as a supplement, be cooled by infusing the balloon 64 with a cooling fluid or other medium.

After cooling the annuloplasty ring 12, the distal end portion 54 of the electrical lead 52 is positioned about the expandable support member 28 so that the electrical lead and the securing member 58 are slidably received near the tip portion 38 of one wing member 36. The constraining wire 42 is pulled tight, which results in the wing members 38 bending radially inward from their convex cross-sectional shape to the flatter cross-sectional shape of FIG. 7. The delivery capsule 48 is then placed over the balloon 64 and the annuloplasty ring 12. Inside the capsule 48, the hook members 44 are bent upward in the proximal direction B. The apparatus 10 is then loaded into a 16 to 22 French catheter (not shown) in a known manner.

The apparatus 10 is introduced into the right jugular vein (not shown) using a known percutaneous technique called the Seldinger technique, and is advanced through the superior vena cava (not shown) to approach the right atrium. The catheter is then passed through the interatrial septum (not shown) to reach the left atrium. Inside the left atrium, the apparatus 10 is positioned just above the mitral valve 14 as is shown in FIG. 7.

Figure 8:
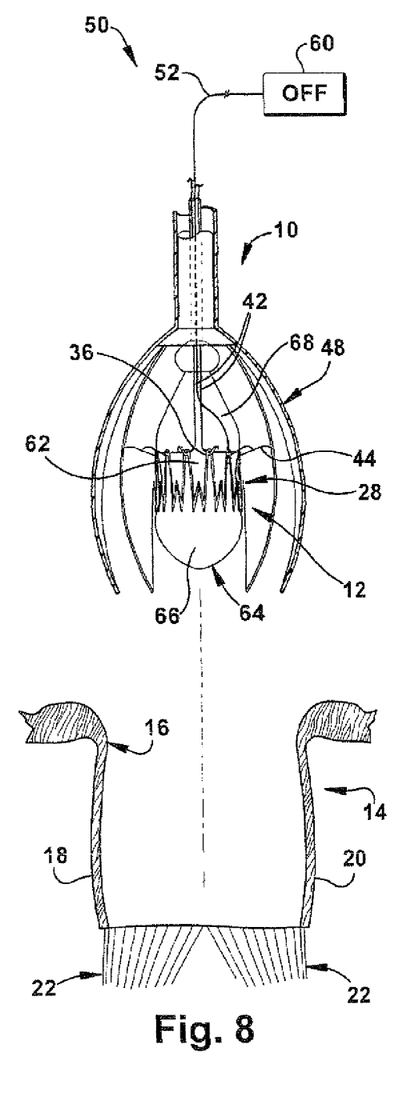
FIG. 8 is a side view similar to FIG. 7 illustrating the apparatus at a subsequent stage of delivery.
Figure 9:
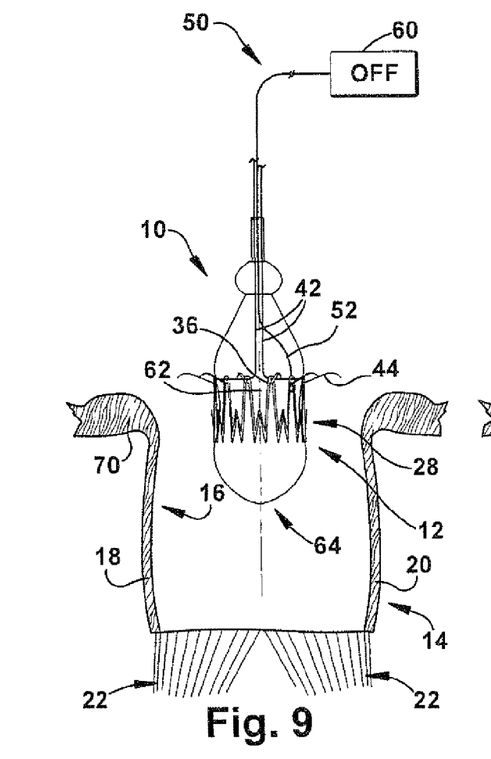
FIG. 9 is a side view similar to FIG. 8 illustrating the apparatus at another subsequent stage of delivery.

Next, the delivery capsule 48 is opened, which exposes the balloon 64 and the annuloplasty ring 12, and also allows the hook members 44 to spring back to the position illustrated in FIG. 8. The balloon 64 is then advanced distally into the annulus 16 of the mitral valve 14 until the center section 62 of the balloon 64 (where the annuloplasty ring 12 is positioned) is at the level of the annulus, as shown in FIG. 8.

Figure 10:
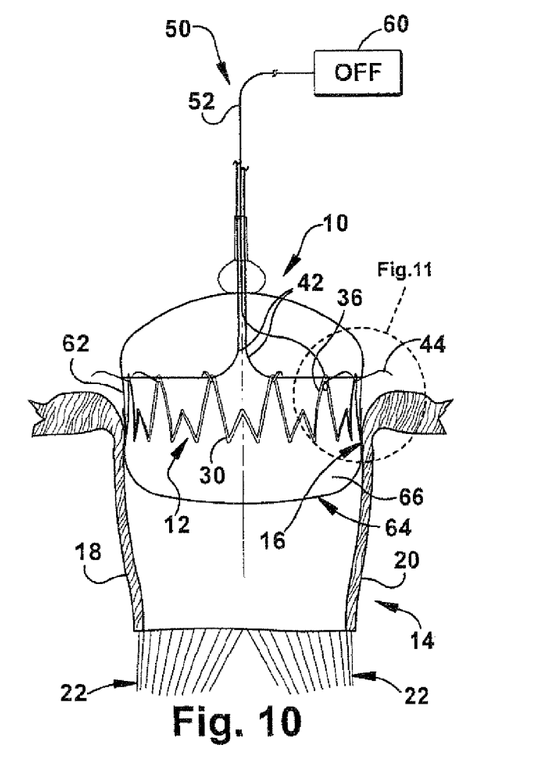
FIG. 10 is a side view similar to FIG. 9 illustrating the annuloplasty ring being deployed in the valve annulus by expansion of a balloon.
Figure 11:
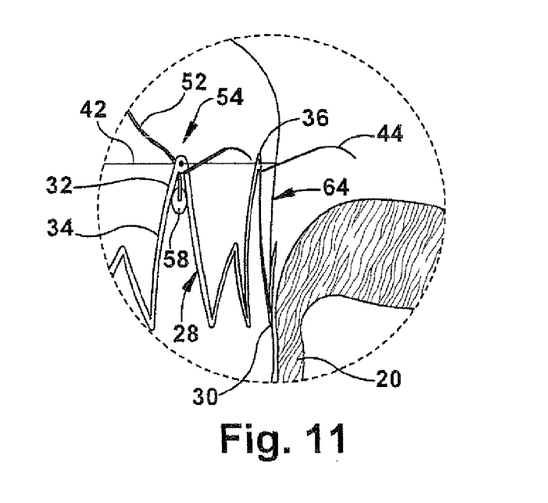
FIG. 11 is an enlarged view of a portion of FIG. 10.

Next, the balloon 64 is inflated to radially expand the annuloplasty ring 12 into full and complete engagement with the valve annulus 16. While the balloon 64 is inflating, the first bulb section 66 pushes the valve leaflets 18 and 20 back to protect the leaflets during expansion of the expandable support member 28. The constraining wire 42 is loosed slightly to compensate for the growing diameter of the expanding balloon 64, but the wire is not completely released. This keeps the wing members 36 held against the balloon 64 for the time being, and also keeps the hook members 44 pointed above the level of the valve annulus 16. The balloon 64 is inflated to the point where the ring 12 is over-expanded in order to ensure full and complete engagement with diseased/dilated annulus 16. As is illustrated in FIGS. 10 and 11, this full annular engagement of the distal end portion 30 of the expandable support member 28 ensures that the annuloplasty ring 12 seats against the inside of the valve annulus 16 and forms a point of fixation for the annuloplasty ring.

Figure 12:
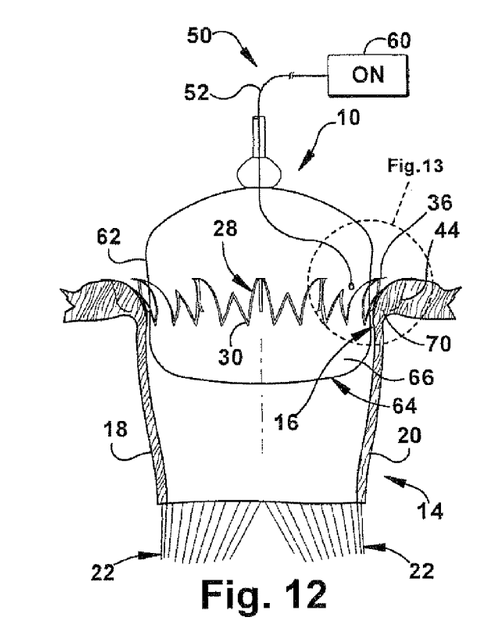
FIG. 12 is a side view similar to FIG. 10 illustrating a further step in the deployment of the annuloplasty ring.
Figure 13:
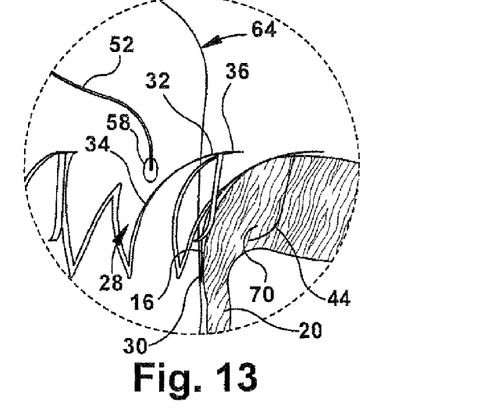
FIG. 13 is an enlarged view of a portion of FIG. 12.

The constraining wire 42 is then released, which allows the main body portion 34 and the wing members 36 of the expandable support member 28 to spring back to their convex shape as shown in FIG. 12. As the wing members 36 bend radially outward, the hook members 44 swing downward in the distal direction A and embed into the cardiac wall 70 and the valve annulus 16. The embedded hook members 44 thus extend distally from the wing members 36 into the cardiac wall 70 to provide the primary point of fixation for the annuloplasty ring 12. As shown in FIG. 13, the convex shape of the expandable support member 28 conforms to the concave shape of the valve annulus 16 and the annuloplasty ring 12 becomes clamped in the annulus between the distal end portion 30 of the expandable support member and the distally extending hook members 44.

FIGS. 12 and 13 also illustrate the process whereby electrical energy is delivered to the expandable support member 28 to raise the temperature of the expandable support member above the pre-determined transition range. In FIG. 12, for example, the energy delivery source 60 is activated to deliver electric current to the electrical lead 52. Electric current can be delivered to the electrical lead 52 at about 0.5 Amps to about 5 Amps, and more preferably at about 1 Amp to about 2 Amps. The electric current delivered to the expandable support member 28 causes the temperature of the expandable support member to rise above the pre-determined transition range. Raising the temperature of the expandable support member 28 above the predetermined transition range causes the annuloplasty ring 12 to contract, which reduces the size of the opening of the valve annulus 16 to a predetermined size and shape defined by the second configuration of the expandable support member. It should be noted that the constriction of the annuloplasty ring 12 to the predetermined size reduces the posterior portion of the annulus 16 but maintains the desired inter-trigonal distance X as another mechanism of fixation.

Figure 14:
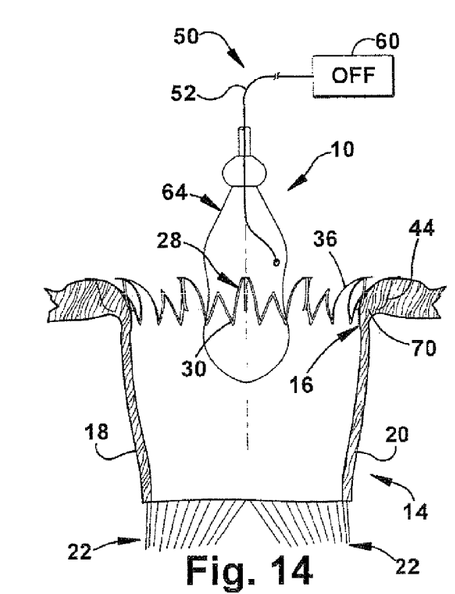
FIG. 14 is a side view similar to FIG. 12 illustrating the annuloplasty ring implanted in the valve annulus with the balloon deflated.
Figure 15:
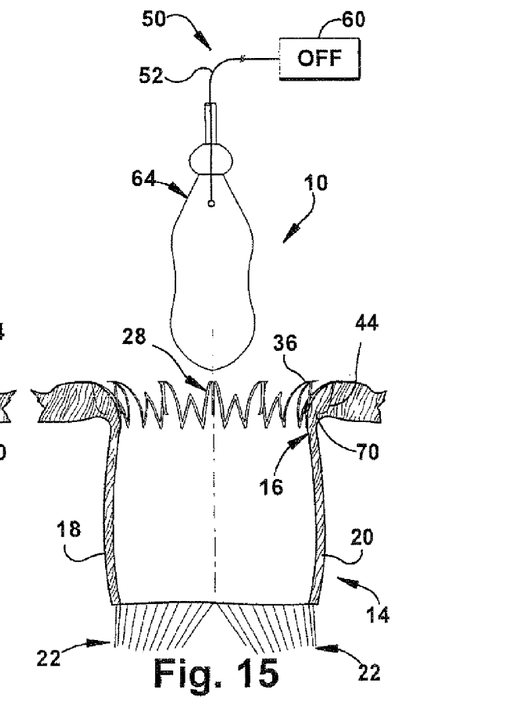
FIG. 15 is a side view similar to FIG. 14 illustrating the constricting effect that the shape memory material of the annuloplasty ring has on the valve annulus.

Finally, as shown in FIGS. 14 and 15, the energy delivery source 60 is deactivated and the balloon 64 deflated and moved out of the valve annulus 16 along with the electrical lead 52. The constriction of the annuloplasty ring 12 due to the shape memory material of the expandable support member 28 thus re-establishes the size of the valve annulus 16 to normal. The flexibility of the expandable support member 28 allows the annuloplasty ring 12 to follow the native shape and contour of the valve annulus 16, yet provide structural support for the annulus which improves the coaptation of the native leaflets 18 and 20 and restores normal valve 14 function.

Before the balloon 64, the constraining wire 42, and the electrical lead 52 are completely withdrawn, the competency of the remodeled valve 14 can be tested by echocardiogram. If necessary, the annuloplasty ring 12 can be re-positioned by tightening the constraining wire 42 to pull the wing members 36 and the hook members 44 upward and out of the cardiac wall 70 and the annulus 16, and then re-inflating the balloon 64 to re-acquire the annuloplasty ring. If the echocardiogram shows the valve repair to be successful, then the constraining wire 42 is pulled out of the apertures 40 in the hook members 44 and the rest of the apparatus 10, including the balloon 64 and the electrical lead 52, is removed from the atrial chamber.

The present invention thus allows for the annuloplasty ring 12 to be delivered in a cardiac catheterization laboratory with a percutaneous approach under local anesthesia using fluoroscopic as well as echocardiographic guidance, thereby avoiding general anesthesia and highly invasive open heart surgery techniques. This approach offers tremendous advantages for high risk patients with severe valvular regurgitation. It should be understood, however, that the present invention contemplates various other approaches, including standard open heart surgeries as well as minimally invasive surgical techniques. Because the present invention omits stitching of the annuloplasty ring 12 in the valve annulus 16, surgical time is reduced regardless of whether an open or percutaneous approach is used.

The technique for implanting the annuloplasty ring 12 in the tricuspid valve follows the same steps described above for the mitral valve 14, except that all of the delivery and implantation steps for a tricuspid annuloplasty ring take place inside the right atrium and on a dilated native tricuspid valve. The annuloplasty ring 12 disclosed herein is capable of achieving an adjustable restriction in a deeper portion of the posterior leaflet segment and in a small portion of the adjacent anterior leaflet. The septal leaflet segment is not usually required to be shortened, so the tricuspid valve annuloplasty ring improves leaflet coaptation and valve function by restriction of the anterior and posterior portions of the native valve tricuspid annulus.

Another embodiment of the present invention is illustrated in FIGS. 16-25. The apparatus $10_a$ shown in FIGS. 16-25 is identically constructed as the apparatus 10 shown in FIG. 3, except as described below. In FIGS. 16-25, structures that are identical as structures in FIG. 3 use the same reference numbers, whereas structures that are similar but not identical carry the suffix "a".

Figure 16A:
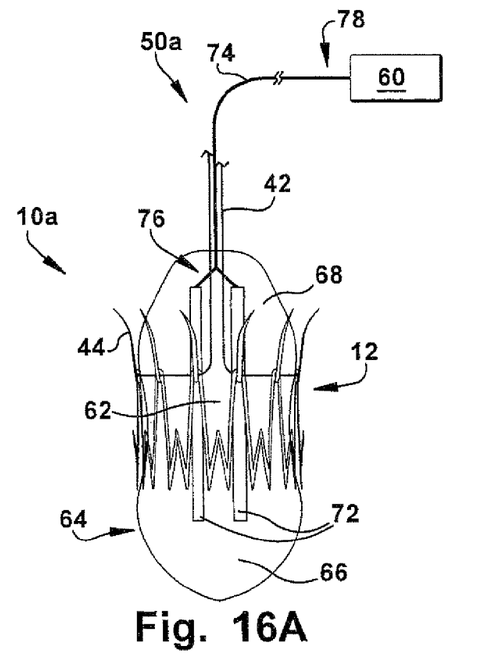
FIG. 16A is a cross-sectional view illustrating another embodiment of an annuloplasty ring (prior to expansion by a balloon) constructed in accordance with the present invention.
Figure 16B:
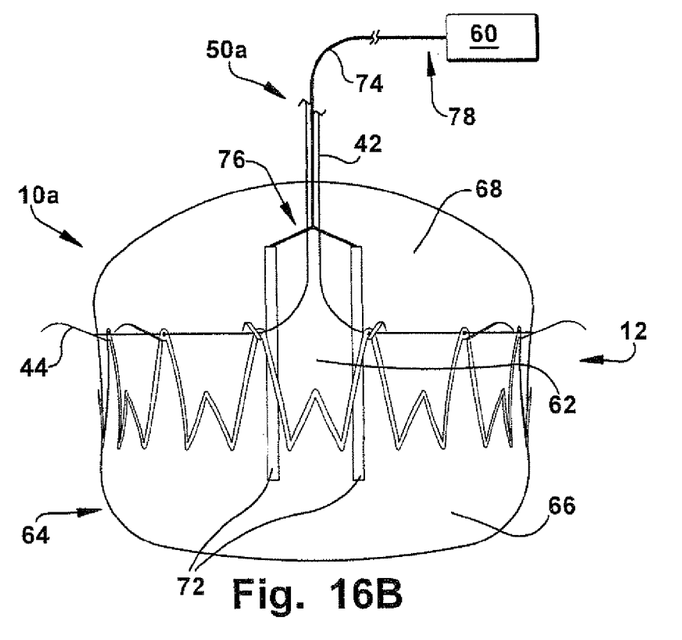
FIG. 16B is a cross-sectional view of the annuloplasty ring in FIG. 16A after expansion by a balloon.

As shown in FIGS. 16A-B, an apparatus $10_a$ for repairing a cardiac valve 14 comprises an annuloplasty ring 12 including an expandable support member 28 having oppositely disposed distal and proximal end portions 30 and 32 and a main body portion 34 between the end portions. The proximal end portion 32 of the expandable support member 28 comprises a plurality of wing members 36 that extend from the main body portion 34. Each of the wing members 36 include at least one hook member 44 for embedding into a cardiac wall 70 and the valve annulus 16 to secure the annuloplasty ring 12 in the annulus of the cardiac valve 14. As shown in FIGS. 16A-B, the apparatus 10, includes a releasable constraining wire 42 for temporarily holding the wing members 36 in a flatter cross-sectional shape during delivery and placement of the annuloplasty ring 12.

The apparatus $10_a$ further comprises an inflatable balloon 64 for expanding the annuloplasty ring 12 into full and complete contact with the annulus 16 of the cardiac valve 14. The inflatable balloon 64 has an hourglass shape defined by first and second bulb sections 66 and 68 connected by a center section 62. Each of these sections 62, 66 and 68 may have a D-shaped diameter (or other shaped diameter) to match the D-shaped diameter of the valve 14 and the annuloplasty ring 12. The center section 62 of the balloon 64 has a smaller diameter than the bulb sections 66 and 68. The first and second bulb sections 66 and 68 and the center section 62 may be inflated together or separately. Further, the sections 62, 66 and 68 may have multiple chambers to accommodate multiple fluids (i.e., an inflation fluid and a cooling fluid).

As shown in FIGS. 16A-B, the apparatus 10, also includes an energy delivery mechanism 50$_a$ for selectively contracting the annuloplasty ring 12 and thereby restricting the valve annulus 16 to support the annulus and correct valvular insufficiency. The energy delivery mechanism 50$_a$ includes two oppositely disposed energy delivery members 72 operably secured to the inflatable balloon 64. The energy delivery members 72 are operably secured to the balloon 64 such that a portion of each of the energy delivery members is in contact with a portion of the expandable support member 28.

The energy delivery members 72 can be operably secured to the balloon 64 using a suitable adhesive or tape, for example. The energy delivery members 72 are made of an electrically conductive material, such as platinum, for example, and have an elongated rectangular shape. It will be appreciated that any number of energy delivery members 72 may be operably secured to the balloon 64 and, further, that the energy delivery members can have any suitable shape, such as a circular or ovoid shape, for example. It will be further appreciated that the energy delivery members 72 may also be disposed about the inflatable balloon 64 in any desired configuration. For example, the energy delivery members 72 may be arranged such that one energy delivery member is disposed about the inflatable balloon 64 approximately 180° from the other energy delivery member.

The energy delivery mechanism 50, further includes at least one electrical lead 74 for conveying electrical energy from an energy delivery source 60 to the electrical delivery members 72. The electrical lead 74 comprises an electrically conductive wire having distal and proximal end portions 76 and 78. As shown in FIGS. 16A-B, the distal end portion 76 of the electrical lead 74 has a spliced or Y-shaped configuration and is operably connected to each of the energy delivery members 72. It will be appreciated, however, that the distal end portion 76 of the electrical lead 74 may have any other configuration suitable to ensure delivery of electrical energy to the electrical delivery members 72.

The proximal end portion 78 of the electrical lead 74 is operably connected to the energy delivery source 60. Examples of suitable energy delivery sources 60 include sources capable of delivering RF energy, x-ray energy, microwave energy, ultrasonic energy such as focused ultrasound, high intensity focused ultrasound energy, light energy, electric field energy, magnetic energy, combinations of the same, or the like. As described in more detail below, activation of the energy delivery source 60 causes an electrical current to be conducted through the electrical lead 74 and into the energy delivery members 72 and the expandable support member 28. This causes the temperature of the expandable support member 28 to rise above the pre-determined transition range so that the expandable support member obtains the second configuration.

To repair the mitral valve 14 with the apparatus 10, using a percutaneous (or intravascular) approach, the annuloplasty ring 12 is properly sized for the mitral valve by the surgical team using fluoroscopic and/or echocardiographic data. The annuloplasty ring 12 may be cooled using a cryogenic source or other suitable means to place the expandable support member 28 in its first configuration. The annuloplasty ring 12 is then positioned about the center section 62 of the balloon 64. It is contemplated that the annuloplasty ring 12 could alternatively, or as a supplement, be cooled by infusing the balloon 64 with a cooling fluid or other medium. The constraining wire 42 is pulled tight, which results in the wing members 36 bending radially inward from their convex cross-sectional shape to the flatter cross-sectional shape of FIG. 17. A delivery capsule 48 is then placed over the balloon 64 and the annuloplasty ring 12. Inside the capsule 48, the hook members 44 are bent upward in the proximal direction B. The apparatus 10, is then loaded into a 16 to 22 French catheter (not shown) in a known manner.

Figure 17:
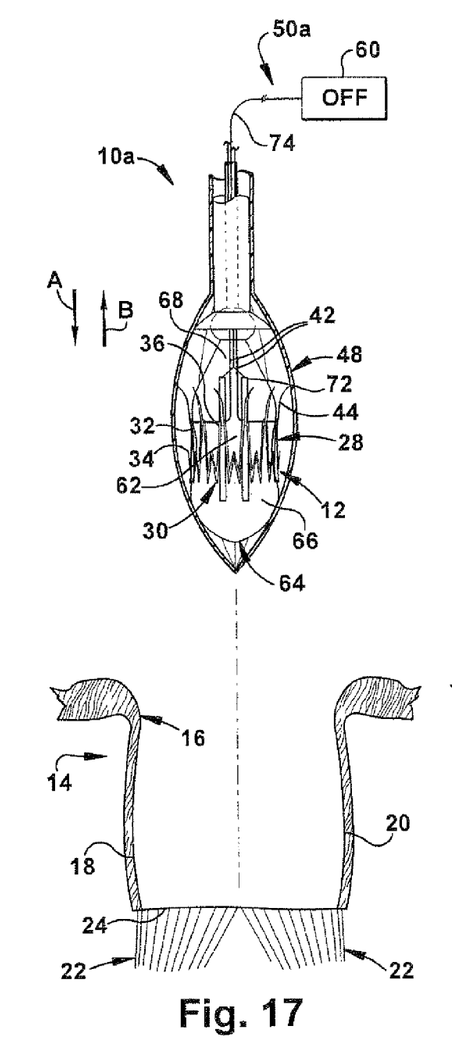
FIG. 17 is a side view, partly in section, of an apparatus for repairing a cardiac valve comprising the annuloplasty ring of FIGS. 16A-B, the apparatus being shown at an initial stage of delivery into an atrial chamber.

The apparatus 10, is introduced into the right jugular vein using a known percutaneous technique, called the Seldinger technique, and is advanced through the superior vena cava to approach the right atrium. The catheter is then passed through the interatrial septum to reach the left atrium. Inside the left atrium, the apparatus 10$_a$ is positioned just above the mitral valve 14 as is shown in FIG. 17.

Figure 18:
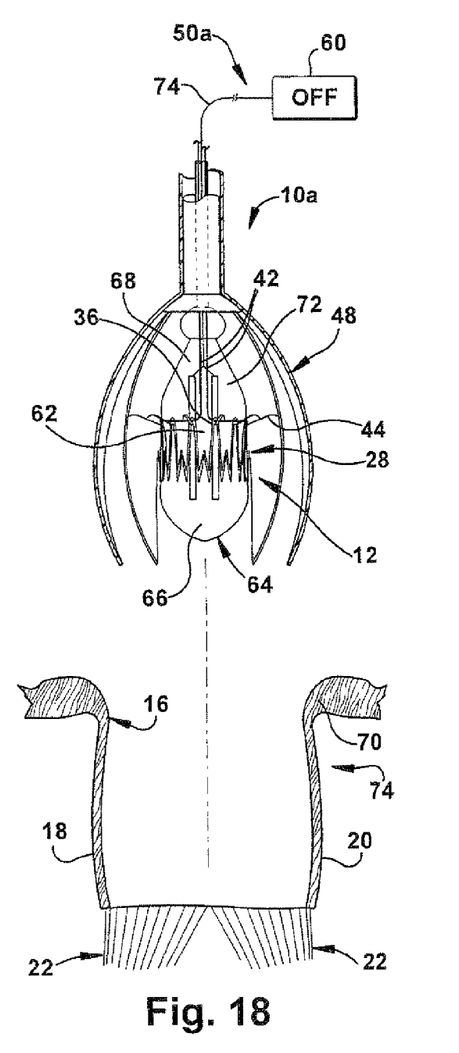
FIG. 18 is a side view similar to FIG. 17 illustrating the apparatus at a subsequent stage of delivery.
Figure 19:
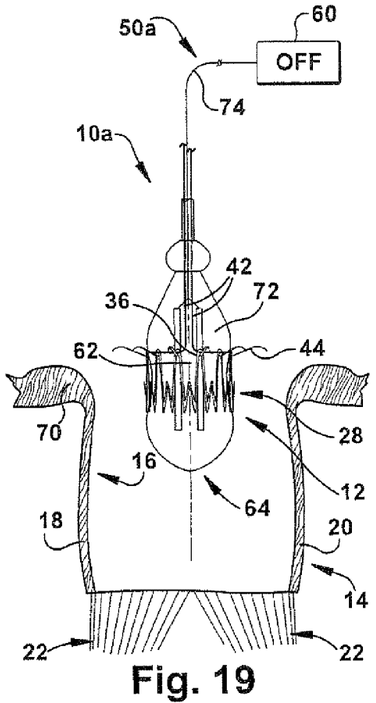
FIG. 19 is a side view similar to FIG. 18 illustrating the apparatus at another subsequent stage of delivery.

Next, the delivery capsule 48 is opened, which exposes the balloon 64 and the annuloplasty ring 12, and also allows the hook members 44 to spring back to the position illustrated in FIG. 18. The balloon 64 is then advanced distally into the annulus 16 of the mitral valve 14 until the center section 62 of the balloon 64 (where the annuloplasty ring 12 is positioned) is at the level of the annulus, as shown in FIG. 19.

Figure 20:
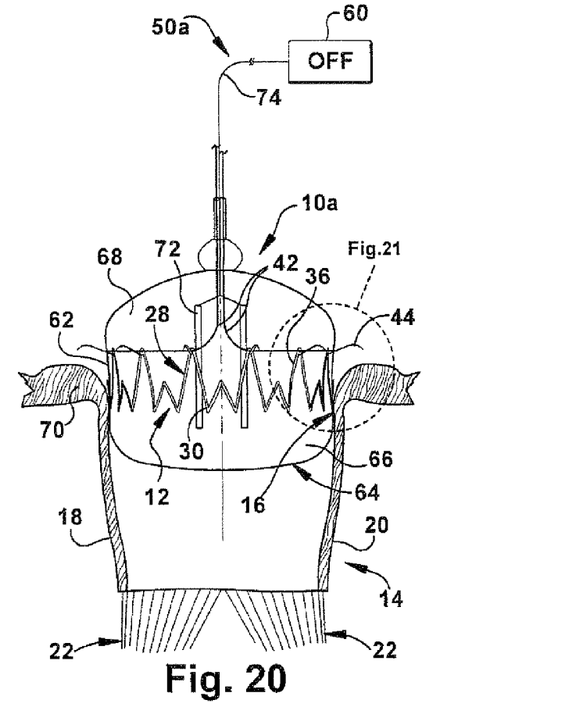
FIG. 20 is a side view similar to FIG. 19 illustrating the annuloplasty ring being deployed in the valve annulus by expansion of a balloon.
Figure 21:
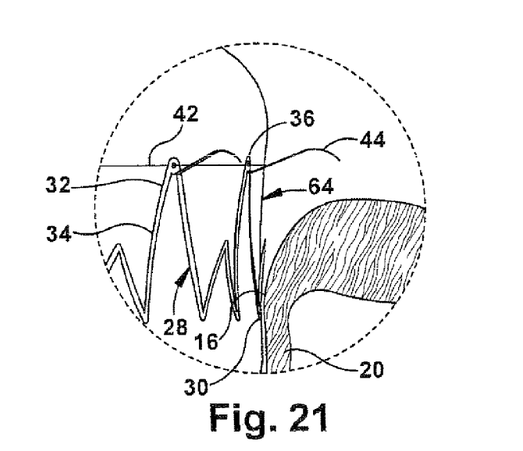
FIG. 21 is an enlarged view of a portion of FIG. 20.

Next, the balloon 64 is inflated to radially expand the annuloplasty ring 12 into full and complete engagement with the valve annulus 16. When the balloon 64 is inflating, the first bulb section 66 pushes the valve leaflets 18 and 20 back to protect the leaflets during expansion of the expandable support member 28. The constraining wire 42 is loosed slightly to compensate for the growing diameter of the expanding balloon 64, but the wire is not completely released. This keeps the wing members 36 held against the balloon 64 for the time being, and also keeps the hook members 44 pointed above the level of the valve annulus 16. The balloon 64 is inflated to the point where the annuloplasty ring 12 is over-expanded in order to ensure full and complete engagement with diseased/dilated annulus 16. As is illustrated in FIGS. 20 and 21, this full annular engagement of the distal end portion 30 of the expandable support member 28 ensures that the annuloplasty ring 12 seats against the inside of the valve annulus 16 and forms a point of fixation for the annuloplasty ring.

Figure 22:
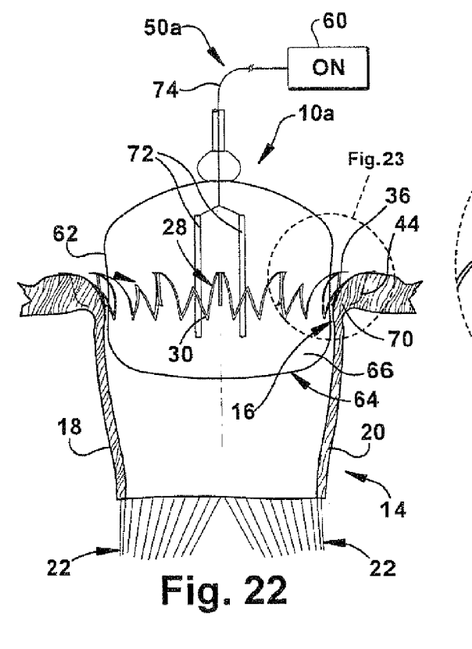
FIG. 22 is a side view similar to FIG. 20 illustrating a further step in the deployment of the annuloplasty ring.
Figure 23:
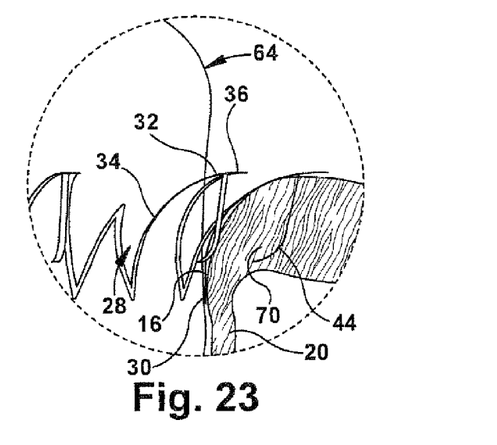
FIG. 23 is an enlarged view of a portion of FIG. 22.

The constraining wire 42 is then released, which allows the main body portion 34 and the wing members 36 of the expandable support member 28 to spring back to their convex shape as shown in FIG. 22. As the wing members 36 bend radially outward, the hook members 44 swing downward in the distal direction A and embed into the cardiac wall 70 and the valve annulus 16. The embedded hook members 44 thus extend distally from the wing members 36 into the cardiac wall 70 to provide the primary point of fixation for the annuloplasty ring 12. As shown in FIG. 23, the convex shape of the expandable support member 28 conforms to the concave shape of the valve annulus 16 and the annuloplasty ring 12 becomes clamped in the annulus between the distal end portion 30 of the expandable support member and the distally extending hook members 44.

FIGS. 22 and 23 also illustrate the process whereby electrical energy is delivered to the expandable support member 28 to raise the temperature of the expandable support member above the pre-determined transition range. In FIG. 22, for example, the energy delivery source 60 is activated to deliver electric current to the electrical lead 74. Electric current can be delivered to the electrical lead 74 at about 0.5 Amps to about 5 Amps and, more preferably, at about 1 Amp to about 2 Amps. The electric current delivered to the expandable support member 28 causes the temperature of the expandable support member to rise above the pre-determined transition range. Raising the temperature of the expandable support member 28 above the transition range causes the annuloplasty ring 12 to contract, which reduces the size of the opening of the valve annulus 16 to a predetermined size and shape defined by the second configuration of the expandable support member. It should be noted that the constriction of the annuloplasty ring 12 to the predetermined size reduces the posterior portion of the annulus 16 but maintains the desired inter-trigonal distance X as another mechanism of fixation.

Figure 24:
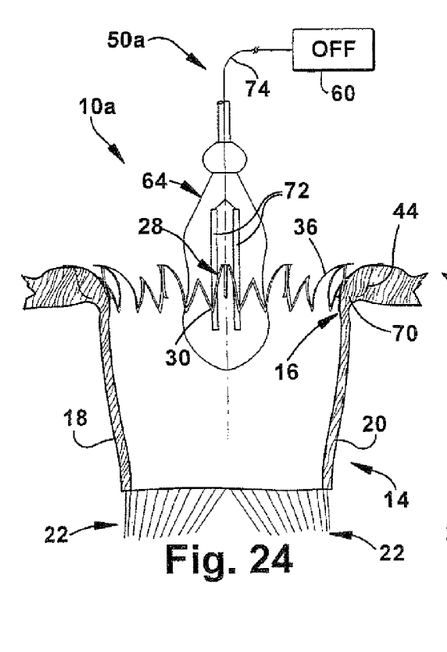
FIG. 24 is a side view similar to FIG. 22 illustrating the annuloplasty ring implanted in the valve annulus with the balloon deflated.
Figure 25:
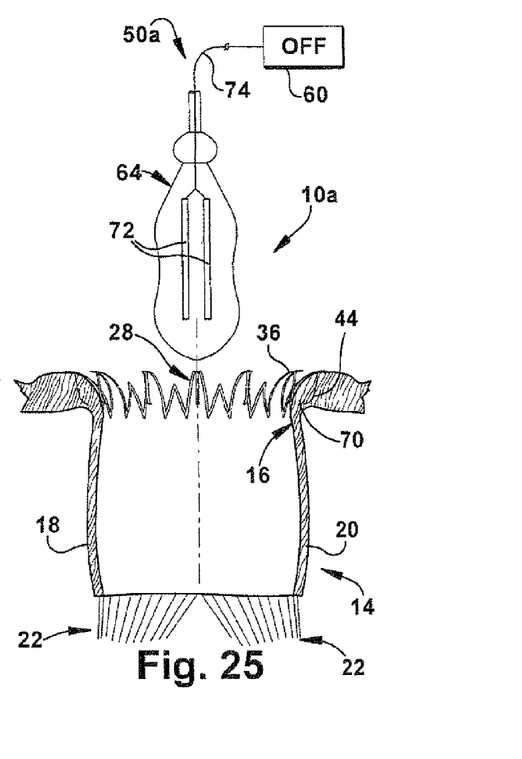
FIG. 25 is a side view similar to FIG. 24 illustrating the constricting effect that the shape memory material of the annuloplasty ring has on the valve annulus.

Finally, as shown in FIGS. 24 and 25, the energy delivery source 60 is deactivated and the balloon 64 deflated and moved out of the valve annulus 16. The constriction of the annuloplasty ring 12 due to the shape memory material of the expandable support member 28 thus re-establishes the size of the valve annulus 16 to normal. The flexibility of the expandable support member 28 allows the annuloplasty ring 12 to follow the native shape and contour of the valve annulus 16, yet provide structural support for the annulus which improves the coaptation of the native leaflets 18 and 20 and restores normal valve 14 function.

Before the balloon 64 and the constraining wire 42 are completely withdrawn, the competency of the remodeled valve 14 can be tested by echocardiogram. If necessary, the annuloplasty ring 12 can be re-positioned by tightening the constraining wire 42 to pull the wing members 36 and the hook members 44 upward and out of the cardiac wall 70 and the annulus 16, and then re-inflating the balloon 64 to re-acquire the annuloplasty ring. If the echocardiogram shows the valve repair to be successful, then the constraining wire 42 is pulled out of the apertures 40 in the hook members 44 and the rest of the apparatus $10_a$, including the balloon 64, is removed from the atrial chamber.

From the above description of the invention, those skilled in the art will perceive improvements, changes and modifications. For example, it is contemplated that, in addition to the balloon-based invention disclosed herein, a mechanical-based apparatus (not shown) capable of maintaining an electrical connection could be used to deliver and deploy the annuloplasty ring 12 described herein. Additionally, it will be appreciated that electrical energy may be delivered wirelessly to the annuloplasty ring 12 using, for example, RF energy. Such improvements, changes and modifications within the skill of the art are intended to be covered by the appended claims.

Having described the invention, we claim:

1. An apparatus for repairing a cardiac valve, said apparatus comprising:
    an annuloplasty ring including an expandable support member having oppositely disposed proximal and distal end portions and a main body portion between said end portions, said proximal end portion of said expandable support member comprising a plurality of wing members that extend from said main body portion;
    each of said wing members including at least one hook member for embedding into a cardiac wall and the valve annulus to secure said annuloplasty ring in the annulus of the cardiac valve; and
    an energy delivery mechanism for selectively contracting said annuloplasty ring and thereby restricting the valve annulus to support the annulus and correct valvular insufficiency, said energy delivery mechanism including a detachable electrical lead having distal and proximal end portions, said distal end portion having a securing member for operably attaching said distal end portion to a portion of said expandable support member and said proximal end portion being operably connected to an energy delivery source.

2. The annuloplasty ring of claim 1 wherein said hook members, when embedded into the cardiac wall and the valve annulus, extend distally from said wing members.

3. The apparatus of claim 1 further comprising a layer of biocompatible material covering at least a portion of said distal end portion and said main body portion of said expandable support member.

4. The apparatus of claim 1 wherein said expandable support member is made from a shape memory material that is responsive to changes in temperature above and below a predetermined temperature transition range, said expandable support member having a first configuration when the temperature is below said predetermined temperature transition range, said expandable support member having a second configuration when heated above said predetermined temperature transition range.

5. The apparatus of claim 4 wherein said expandable support member is insertable into the annulus of the cardiac valve in said first configuration and is thereafter heatable above said predetermined temperature transition range to change said expandable support member into said second configuration, wherein movement of said expandable support member into said second configuration causes a reduction in size of the opening defined by the valve annulus.

6. The apparatus of claim 1 wherein said inflatable balloon has an hourglass shape defined by first and second bulb sections connected by a center section having a smaller diameter than said bulb sections, said annuloplasty ring being positioned about said center section of said inflatable balloon.

7. The apparatus of claim 1 wherein at least a portion of said expandable support member is treated with at least one therapeutic agent for eluting into the blood stream and/or cardiac tissue.

8. The apparatus of claim 1 wherein a plurality of portions of said expandable support member are separately treated with a different one of said at least one therapeutic agent.

9. The apparatus of claim 8 wherein said main body portion and said wing members are each separately treated with a different one of said at least one therapeutic agent.

10. The apparatus of claim 8 wherein each of said wing members is separately treated with a different one of said at least one therapeutic agent.

11. The apparatus of claim 1, wherein each of said hook members extends distally between each of said wing members and a location laterally adjacent said main body portion of said expandable support member.

12. The apparatus of claim 1, further including at least one constraining wire for temporarily holding said wing members in a flattened configuration during deployment of said apparatus.

13. An apparatus for repairing a cardiac valve, said apparatus comprising:
    an annuloplasty ring including an expandable support member having oppositely disposed proximal and distal end portions and a main body portion between said end portions, said proximal end portion of said expandable support member comprising a plurality of wing members that extend from said main body portion;
    each of said wing members including at least one hook member for embedding into a cardiac wall and the valve annulus to secure said annuloplasty ring in the annulus of the cardiac valve; and
    an energy delivery mechanism for selectively contracting said annuloplasty ring and thereby restricting the valve annulus to support the annulus and correct valvular insufficiency, said energy delivery mechanism including a detachable electrical lead having distal and proximal end portions, said distal end portion having a securing member for operably attaching said distal end portion to a portion of said expandable support member and said proximal end portion being operably connected to an energy delivery source;

wherein a layer of biocompatible material covers at least a portion of said distal end portion and said main body portion of said expandable support member.

* * * * *